(12) United States Patent
Olbert et al.

(10) Patent No.: US 7,273,593 B2
(45) Date of Patent: Sep. 25, 2007

(54) REACTOR HAVING A HEAT EXCHANGE MEDIUM CIRCULATION

(75) Inventors: Gerhard Olbert, Dossenheim (DE); Franz Corr, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 524 days.

(21) Appl. No.: 10/197,848

(22) Filed: Jul. 19, 2002

(65) Prior Publication Data

US 2003/0017095 A1 Jan. 23, 2003

(30) Foreign Application Priority Data

Jul. 20, 2001 (DE) ................................ 101 35 498

(51) Int. Cl.
*F28D 21/00* (2006.01)
*F28D 15/00* (2006.01)
*F28F 13/06* (2006.01)
*B32B 27/04* (2006.01)

(52) U.S. Cl. ...................... 422/173; 422/129; 422/138; 422/312; 422/201; 422/202; 422/203; 422/205; 165/104.19; 165/DIG. 228; 165/104.22; 165/104.25; 165/104.28; 165/104.31; 165/108

(58) Field of Classification Search ................ 422/173, 422/167, 200, 138; 415/176, 110, 106, 168.2; 165/159, 157, 145; 384/100
See application file for complete search history.

(56) References Cited

U.S. PATENT DOCUMENTS

| | | | | |
|---|---|---|---|---|
| 2,921,533 A | * | 1/1960 | Williams | ..................... 415/112 |
| 3,434,761 A | * | 3/1969 | Marley | ....................... 384/103 |
| 3,871,445 A | * | 3/1975 | Wanka et al. | .......... 165/104.14 |
| 4,190,396 A | * | 2/1980 | Tomioka et al. | ............. 415/110 |
| 4,505,637 A | * | 3/1985 | Raczynski | ................... 415/112 |
| 4,613,281 A | * | 9/1986 | Lubieniecki | ............. 415/171.1 |
| 4,657,741 A | | 4/1987 | Vogl | |
| 6,747,162 B2 | * | 6/2004 | Olbert et al. | ................ 549/248 |
| 6,756,023 B1 | * | 6/2004 | Corr et al. | ................... 422/198 |
| 2004/0247211 A1 | * | 12/2004 | Hamke | ........................ 384/100 |

FOREIGN PATENT DOCUMENTS

| | | |
|---|---|---|
| DE | 34 09 159 | 9/1985 |
| DE | 198 36 792 | 2/2000 |

OTHER PUBLICATIONS

Perry's Chemical Engineers' Handbook, 1984, McGraw-Hill Book Company, Sixth Edition, p. 6-7 to 6-8.*

* cited by examiner

*Primary Examiner*—Glenn Caldarola
*Assistant Examiner*—Kaity Handal
(74) *Attorney, Agent, or Firm*—Oblon, Spivak, McClelland, Maier & Neustadt, P.C.

(57) ABSTRACT

A reactor including a bundle of catalyst tubes through which a reaction mixture is passed, and wherein a heat exchange medium is passed through a space surrounding the catalyst tubes and including ring lines at both reactor ends with jacket orifices for feeding in and removing the heat exchange medium by at least one pump. The heat exchange medium is fed to the upper ring line and is sucked in via the lower ring line by the at least one pump having at least one vertical pump shaft mounted and operated at its upper end. The at least one pump includes a diagonal rotor and a restrictor gap in the longitudinal direction of the at least one pump shaft, within the heat exchange medium, on the pressure side of the at least one pump for sealing and mounting the at least one pump shaft and reducing axial shear of the diagonal rotor.

15 Claims, 6 Drawing Sheets

REACTOR HAVING A HEAT EXCHANGE MEDIUM CIRCULATION

BACKGROUND OF THE INVENTION

1. Field of the Invention

The present invention relates to a reactor comprising a bundle of catalyst tubes, through whose space surrounding the catalyst tubes a heat exchange medium is passed, a pump for circulating the heat exchange medium for a reactor and a use.

2. Discussion of the Background

The conventional design of reactors of the generic type consists of a generally cylindrical container in which a bundle, i.e. a plurality of catalyst tubes is accommodated in a usually vertical arrangement. These catalyst tubes, which, if required, may contain supported catalysts, are tightly fastened at their ends in tube sheets and open in each case into a hood connected at the upper or lower end to the container. The reaction mixture flowing through the catalyst tubes is fed in and removed, respectively, via these hoods. A heat exchange medium circulation is passed through the space surrounding the catalyst tubes, in order to compensate the heat balance, in particular in the case of reactions involving considerable heat of reaction.

For economic reasons, reactors having a very large number of catalyst tubes are used, the number of catalyst tubes accommodated frequently being from 5 000 to 50 000.

Regarding the heat exchange medium circulation, it is known that a substantially homogeneous temperature distribution of the heat exchange medium is desirable in each horizontal section of the reactor, in order as far as possible to involve all catalyst tubes uniformly in the reaction. The supply of heat or removal of heat via external ring lines mounted in each case at the reactor ends and having a plurality of jacket orifices, as described, for example, in DE-B-34 09 159, serves for smoothing the temperature distribution.

It is known that reactors comprising a catalyst tube bundle are advantageously operated by the cocurrent procedure, both reaction mixture and heat exchange medium preferably being fed in at the upper reactor end and being removed from the lower reactor end.

With the countercurrent procedure, cocurrent flow has advantages such as higher throughputs, lower catalyst hotspot temperatures, desired increase in the heat exchange medium temperature in the direction of the final reaction in the catalyst tubes, good temperature uniformity of the heat exchange medium over the reactor cross section, i.e. good horizontal temperature stratification, clearly defined operating states over the height of the catalyst tube space owing to the lack of feedback by the heat exchange medium.

Axial-flow pumps, in particular propeller pumps, which have a vertical pump shaft, and which are mounted and driven at their upper end and thus usually transport the heat exchange medium downward have usually been used to date for circulating the heat exchange medium through the space surrounding the catalyst tubes. A pump arrangement having a vertical pump shaft which is mounted and driven at its lower end has not been realized technically to date, in particular owing to the complicated pump shaft packing required in this case.

DE-A 198 36 792.9 describes a reactor comprising cocurrent flow of reaction mixture and heat exchange medium in a proven arrangement of the pump, having a vertical pump shaft which is mounted and driven at its upper end, and which transports the heat exchange medium downward, where, by arranging a cylindrical partition in each case in the upper and the lower ring line and by using the space between upper and lower ring line for deflecting the heat exchange medium stream, the heat exchange medium of the outer lower ring line is fed, via a region in the space between lower and upper ring line, to the inner upper ring line, and via its jacket orifices to the space surrounding the catalyst tubes, and is removed via jacket orifices into the inner lower ring line and then via a space in the region between lower and upper ring line via the outer upper ring line. This provides a design solution which, with proven transport of the heat exchange medium downward by the pump, ensures flow around the catalyst tubes by the heat exchange medium downward and hence cocurrently with the reaction mixture likewise fed downward through the catalyst tubes. However, this solution requires a reactor adaptation which is complicated in design, in particular a corresponding division of upper and lower ring line and of the space between upper and lower ring line into a plurality of chambers.

SUMMARY OF THE INVENTION

It is an object of the present invention to ensure flow downward around the catalyst tubes of a reactor comprising a bundle of catalyst tubes and hence cocurrently with a reaction mixture likewise fed downward through the catalyst tubes, in a manner which is safe and simple in design, it being possible to convert existing reactors in a simple manner. It is intended here for the heat exchange medium to form a free level in the pump casing, permitting shaft passage from the pump casing at or close to atmospheric pressure. It is a further object of the present invention to smooth the temperature in the heat exchange medium stream taken off from the reactor.

We have found that this object is achieved by a reactor comprising a bundle of catalyst tubes through which a reaction mixture is passed and through whose space surrounding the catalyst tubes a heat exchange medium is passed, comprising ring lines at both reactor ends with jacket orifices for feeding in and removing the heat exchange medium by means of one or more pumps, the heat exchange medium being fed to the upper ring line and being sucked in via the lower ring line by the pump(s) having a vertical pump shaft or vertical pump shafts which is or are mounted and driven at their upper end.

In the present invention, the pump(s) has or have a diagonal rotor and a restrictor gap in the longitudinal direction of the pump shaft(s), within the heat exchange medium, on the pressure side of the pump(s) for sealing and mounting the pump shaft(s) and reducing the axial shear of the diagonal rotor.

According to the invention, one or more pumps, in each case having a vertical pump shaft, are used. Two or four pumps arranged uniformly over the reactor circumference are preferably provided. For greater clarity, the further description always relates to one pump, although, as stated above, it is also entirely possible to provide a plurality of pumps for circulating the heat exchange medium for a single reactor.

The upper end of the pump shaft is mounted and driven in the same way as in the case of the known axial-flow feed pumps, in particular propeller pumps, with transport of the heat exchange medium downward. The mounting is frequently effected by means of two oil- or grease-lubricated bearings.

As usual, the nonrotating (static) part of the pump is referred to as the pump casing.

According to the invention, the pump has, as a feed member, a diagonal rotor, also referred to as semiaxial rotor. Diagonal rotor pumps can be considered as an intermediate stage between axial-flow feed pumps on the one hand and radial-flow feed pumps on the other hand: axial-flow feed pumps are distinguished by substantially identical diameters of the feed organ, in this case generally referred to as propeller, on the pump suction and pressure sides. Radial-flow feed pumps on the other hand have a ratio of the diameter on the pressure side to that on the suction side of from about 5 to 10. The ratio of the diameter on the pressure side to that on the suction side is in the range in between these two extremes for diagonal rotors.

The geometry of the diagonal rotor means that delivery and pumping head for a diagonal rotor pump are in the middle range, whereas an axial-flow feed pump and radial-flow feed pump once again represent the extremes, i.e. the axial-flow feed pump handles large deliveries with a small head whereas radial-flow pumps have large pumping heads but low deliveries.

According to the invention, a pump having a diagonal rotor, i.e. having a rotor with a ratio of the diameter on the pressure side to that on the suction side of from about 1 to 5, is thus used. It has the advantage of good performance, both with respect to delivery and with respect to pumping head, i.e. a delivery of up to 10 000 m$^3$/h and a pumping head of up to about 6-8 m, if the heat exchange medium used is a salt melt, in particular a eutectic salt melt comprising potassium nitrate and sodium nitrite, or up to about 16 m if the heat exchange medium used is a heat transfer oil. Moreover, in the case of the use according to the invention, it has a major advantage that the heat exchange medium is deflected in the pump itself and hence is released directly into the upper ring line.

According to the invention, the pump shaft is not completely sealed off from the heat exchange medium. On the contrary, the seal between the heat exchange medium and the pump shaft is in the form of a leak-permeable restrictor gap. The restrictor gap is arranged in the longitudinal direction of the pump shaft, within the heat exchange medium, on the pressure side of the pump. It performs three functions important for the satisfactory operation of the pump: the sealing of the pump shaft, the mounting of said shaft and the reduction in the axial shear of the diagonal rotor.

The seal, which is leak-permeable according to the invention, leads to a drop in the pressure of the heat exchange medium, and the pressure is thus close to atmospheric pressure at the shaft lead-through. The novel leak-permeable restrictor gap permits a certain leakage stream, which is formed by a part-stream of the heat exchange medium on the pressure side and which is preferably recirculated to the suction side of the pump. A leakage stream of from 2 to 30%, in particular from 5 to 10%, of the total stream of the heat exchange medium is preferably permitted.

The second function of the restrictor gap, the mounting of the pump shaft, enables the pump to be operated at a higher speed and the diagonal rotor to be designed with a smaller diameter, with the result that the pump can circulate larger heat exchange medium streams.

The novel restrictor gap moreover performs the function of reducing the axial shear of the diagonal rotor. This is effected by substantially absorbing the forces active on the diagonal rotor.

The restrictor gap is formed on the pressure side of the pump, in particular immediately after the diagonal rotor, preferably by means of a locally increased shaft diameter and corresponding design of the casing, in such a way that there is a gap in the longitudinal direction of the pump shaft. Here, the restrictor gap is dimensioned in such a way that it performs the three abovementioned functions of sealing, mounting and reduction of axial shear.

Preferably, it is possible to provide grooves in the restrictor gap, in particular on the rotating, i.e. inner, side thereof. In addition or alternatively, it is also possible to form grooves on the outer, static side of the restrictor gap.

Preferably, it is possible to take off a part-stream of the heat exchange medium, in particular from 5 to 50%, preferably from 10 to 20%, of the total stream of the heat exchange medium, from the upper ring line, to pass said part-stream via one or more external heat exchangers and then to feed said part-stream back to the lower ring line.

Particularly preferably, the novel reactor is equipped with baffle plates which are arranged in particular in such a way that they leave a cross section for passage alternately in the middle of the reactor and at the reactor wall. This ensures a substantially uniform flow toward all catalyst tubes over the reactor cross section.

In a preferred embodiment, in addition to the restrictor gap on the pressure side of the pump, which acts inter alia as a hydrodynamic bearing lubricated by heat exchange medium, a further hydrodynamic bearing is provided on the suction side of the pump and is formed, analogously to the restrictor gap, as a leak-permeable seal of the diagonal rotor with respect to the pump casing. As a result of this additional hydrodynamic bearing, the quiet running of the pump is further improved, making it possible further to increase the speed of the pump shaft and hence the achievable delivery.

Preferably, the efficiency of the pump can be further considerably increased, in particular in new designs of reactors, by installing a pump outlet spiral. An efficiency in the region of 75% can thus be achieved.

The novel reactor is preferably operated in such a way that the reaction mixture is passed downward through the catalyst tubes. In this mode, it is possible to mount, on the inlet tube plate, an inert material bed which has a number of positive effects on the procedure: it results in more uniform distribution of the reaction gas mixture over all catalyst tubes of the bundle, and it acts as a dirt trap for dirt particles, in particular solid dirt particles, which may be entrained with the reaction gas mixture and as a flame barrier for preventing a flashback of the reaction gas mixture in the reactor inlet hood in the event of an ignition/explosion in the catalyst tubes. The inert material bed acts as a blow-out protection in the case of a flash or deflagration. In this mode, it is also possible to replace the inert material bed and, if required, the top catalyst layer in a simple manner by partial sucking-up and introduction of fresh materials. If the catalyst cakes in the initially flow-through region of the catalyst tubes, in the present case the upper region, it is possible to remove the damaged catalyst by drilling out.

In this preferred flow-through of the catalyst tubes downward, it is possible, by the novel design of the pump for circulating the heat exchange medium, to ensure the preferred cocurrent flow of reaction mixture and heat exchange medium in a simple manner.

Further preferred embodiments envisage that the diagonal rotor is equipped, on its rear disks, with additional, two or more, about 2 to 10 mm high blades which result in a pressure drop on the pressure side in the direction of the pump shaft. Alternatively or additionally, it is possible, by a suitable design of the rear disk of the diagonal rotor and of the pump casing, to form an axial annular gap having a sealing, mounting and axial shear reducing function.

In connection with one or both of the abovementioned measures, it is moreover possible to provide one or more relief holes through the rear disk of the diagonal rotor from the pressure side to the suction side thereof.

The above-mentioned additional measures, individually or in combination with one another, can form a part of the sealing, mounting and axial shear reducing function of the leak-permeable restrictor gap on the pressure side of the pump, in an extreme case also the complete function, and can thus replace said restrictor gap.

The present invention also relates to a pump for a reactor, having a vertical pump shaft, which is mounted and driven at its upper end, wherein the pump has a diagonal rotor and a restrictor gap in the longitudinal direction of the pump shaft, performing a sealing, mounting and axial shear reducing function.

For the cocurrent flow of reaction mixture and heat exchange medium, which can particularly preferably be achieved by means of the novel reactor, it is particularly advantageous to provide one bypass for the heat exchange medium or preferably a plurality of bypasses for the heat exchange medium which are distributed uniformly over the reactor circumference, in the lower region of the reactor. Consequently, the temperature of the heat exchange medium is particularly advantageously adapted to the temperature profile of the reaction. At the same time, the power requirement of the pump is thus substantially reduced.

The novel reactor is advantageously used for carrying out oxidation reactions, in particular for the preparation of phthalic anhydride, maleic anhydride, glyoxal, (meth)acrolein or (meth)acrylic acid.

The novel reactor thus has the advantage of ensuring, in a manner which is simple in design, transport of the heat exchange medium stream downward in the pump and hence feeding thereof directly into the upper ring line of a reactor. In the case of the likewise preferred passage of the reaction mixture, downward through the catalyst tubes, the advantageous cocurrent flow of the reaction mixture and heat exchange medium is thus achieved.

It is particularly advantageous that, owing to the novel design of the pump, the heat exchange medium is close to or at atmospheric pressure at the shaft lead-through from the pump casing into the atmosphere and that there is therefore no need for any packing on the pump shaft at this point.

Because the feed member is designed as a diagonal rotor, the heat exchange medium is transported directly into the upper ring line of the reactor. A particularly compact design and shorter shaft length compared with known designs with axial-flow feed pumps are thus possible.

Compared with known designs, the pump shaft is shorter, in particular because of the geometrically favorable transport direction of the diagonal rotor directly into the upper ring line and the additional single or preferably double hydrodynamic mounting of the pump shaft. Compared with known axial-flow pumps with downward transport, a certain length of the pump shaft to the upper bearing, about 60%, based on the known axial-flow feed pumps, is still required to ensure raising of the level above the lower edge of the upper tube plate and thus to avoid the admission of air into the reactor and to remove evolved or introduced gas, to ensure absolutely safe, dry shaft lead-through from the pump casing into the atmosphere and moreover to reduce the temperature up to the upper bearing of the pump.

The novel pump can advantageously be designed as a slide-in module for existing plants without complicated design modifications being necessary for this purpose. The piping of an existing external heat exchanger might have to be changed. Particularly advantageous in this context is that the pump can be pushed into the pump casing from above. For this purpose, it is not necessary to drain the heat exchange medium or to provide shut-off valves.

Moreover, the temperature uniformity of the heat exchange medium stream is further improved by the circulation in the novel apparatus.

BRIEF DESCRIPTION OF THE DRAWINGS

The invention is illustrated in more detail below with reference to the drawings.

Specifically.

DESCRIPTION OF THE PREFERRED EMBODIMENTS

Figure 1:
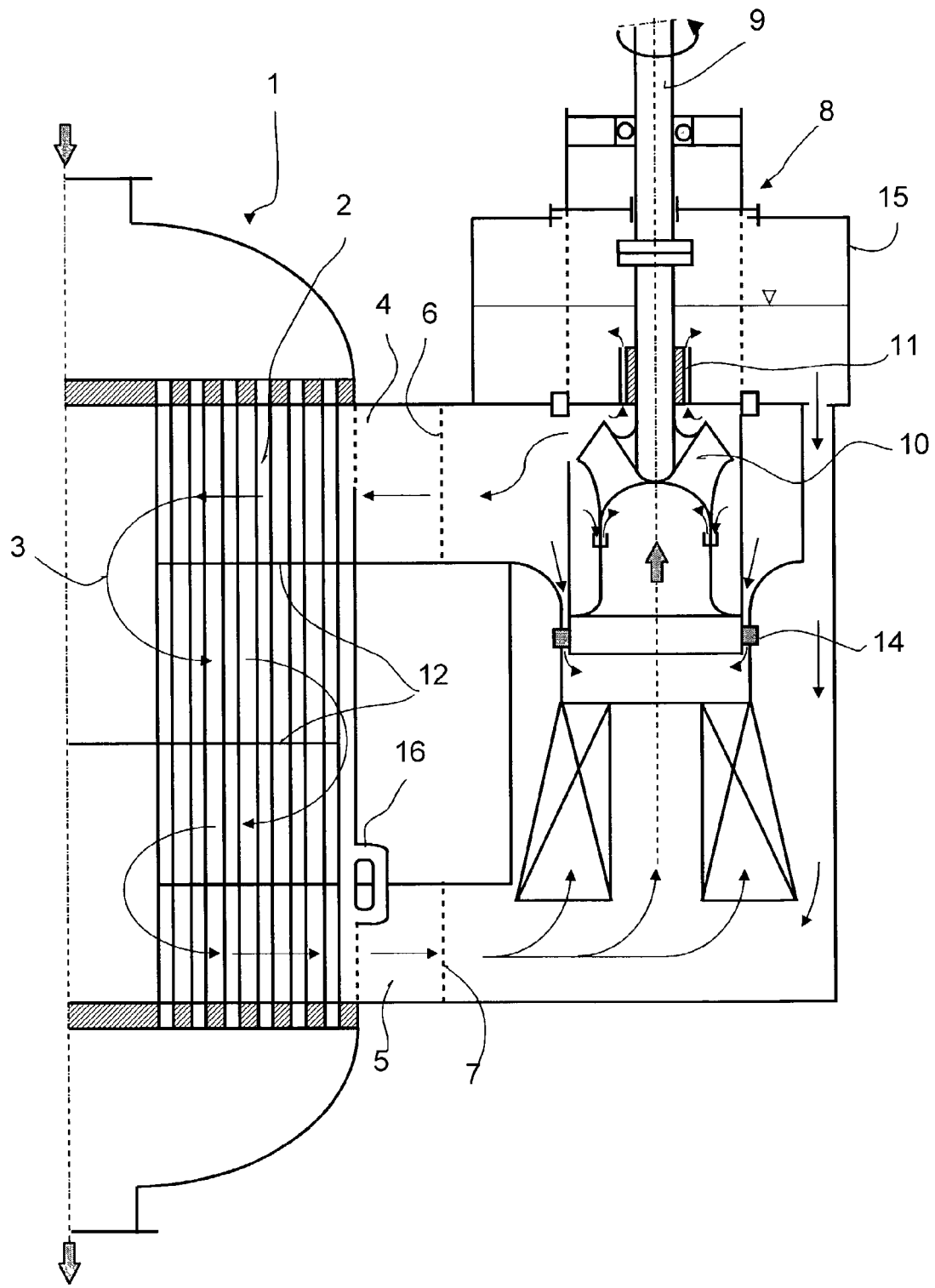
FIG. 1 shows a longitudinal section through an embodiment of a novel reactor, with an additional variant in FIG. 1a, FIG. 2 shows a longitudinal section through a reactor according to the prior art.

The longitudinal sectional view in FIG. 1 shows a reactor 1, comprising a bundle of catalyst tubes 2, comprising a heat exchange medium stream 3 through the space between the catalyst tubes, comprising upper ring line 4 and lower ring line 5, in each case with jacket orifices 6 and 7, respectively, and preferably comprising baffle plates 12. The circulation of the heat exchange medium 3 is effected by means of a pump 8 having a pump casing 15 and having a pump shaft 9 on which a diagonal rotor 10 is arranged and which has a leak-permeable restrictor gap 11, in the longitudinal direction of the pump shaft 9, on the pressure side of the pump 8, and preferably a further hydrodynamic bearing 13 (see FIG. 4), which is likewise in the form of a leak-permeable packing lubricated by means of heat exchange medium. The pump 8 is preferably in the form of a slide-in module, and a slide-in bearing 14 is therefore provided which is preferably sealed by a fit, seals the mutually displaceable sealing surfaces and compensates the thermal expansion of the engaging parts which is due to assembly and operation. A bypass 16 for the heat exchange medium can be arranged in the region of the bottom baffle plate 12, as shown in the drawing.

Figure 1A:
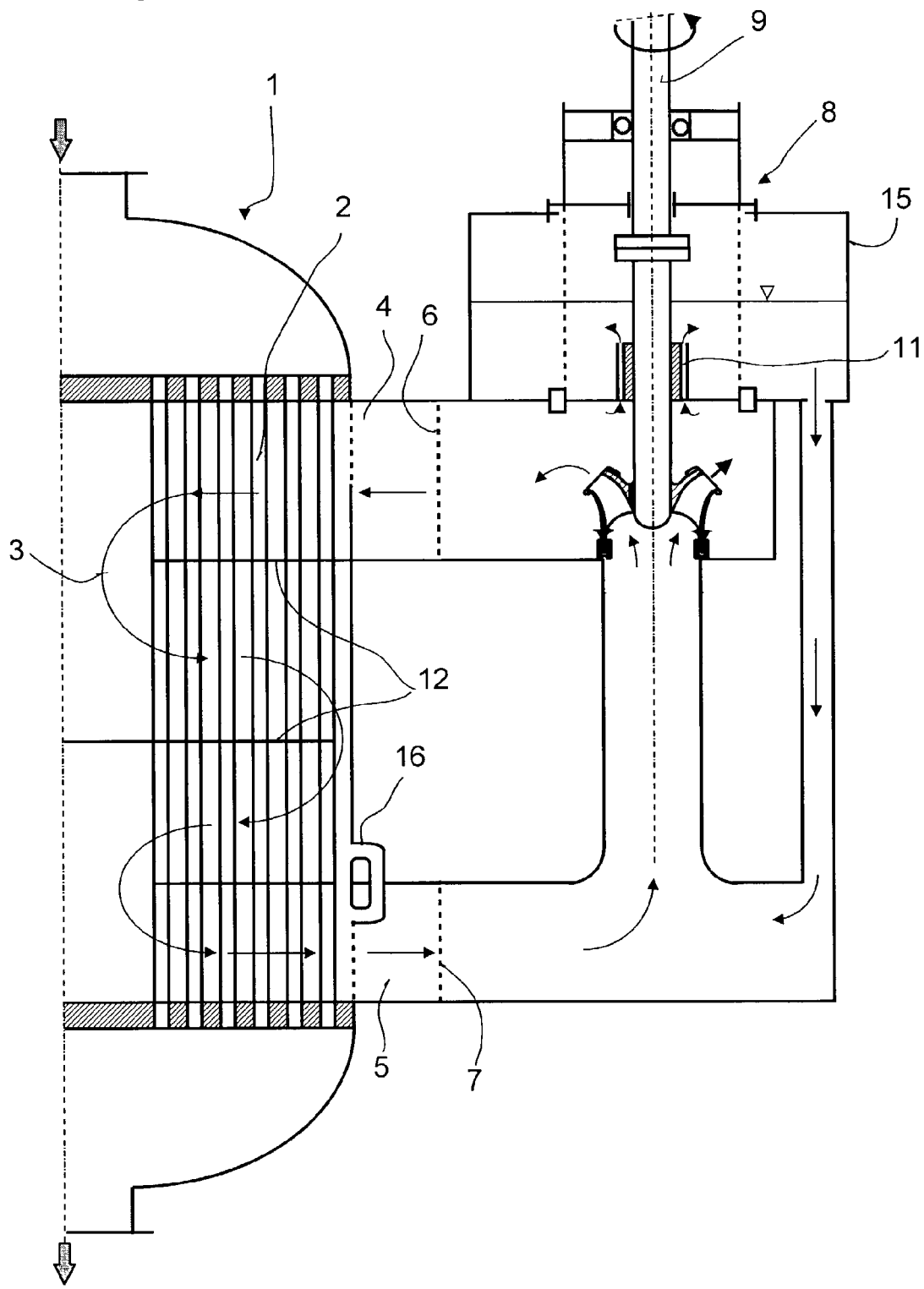

The cross-sectional view in FIG. 1A shows a further variant which differs from the embodiment shown in FIG. 1 in particular in that no slide-bearing 14 is provided.

Figure 2:
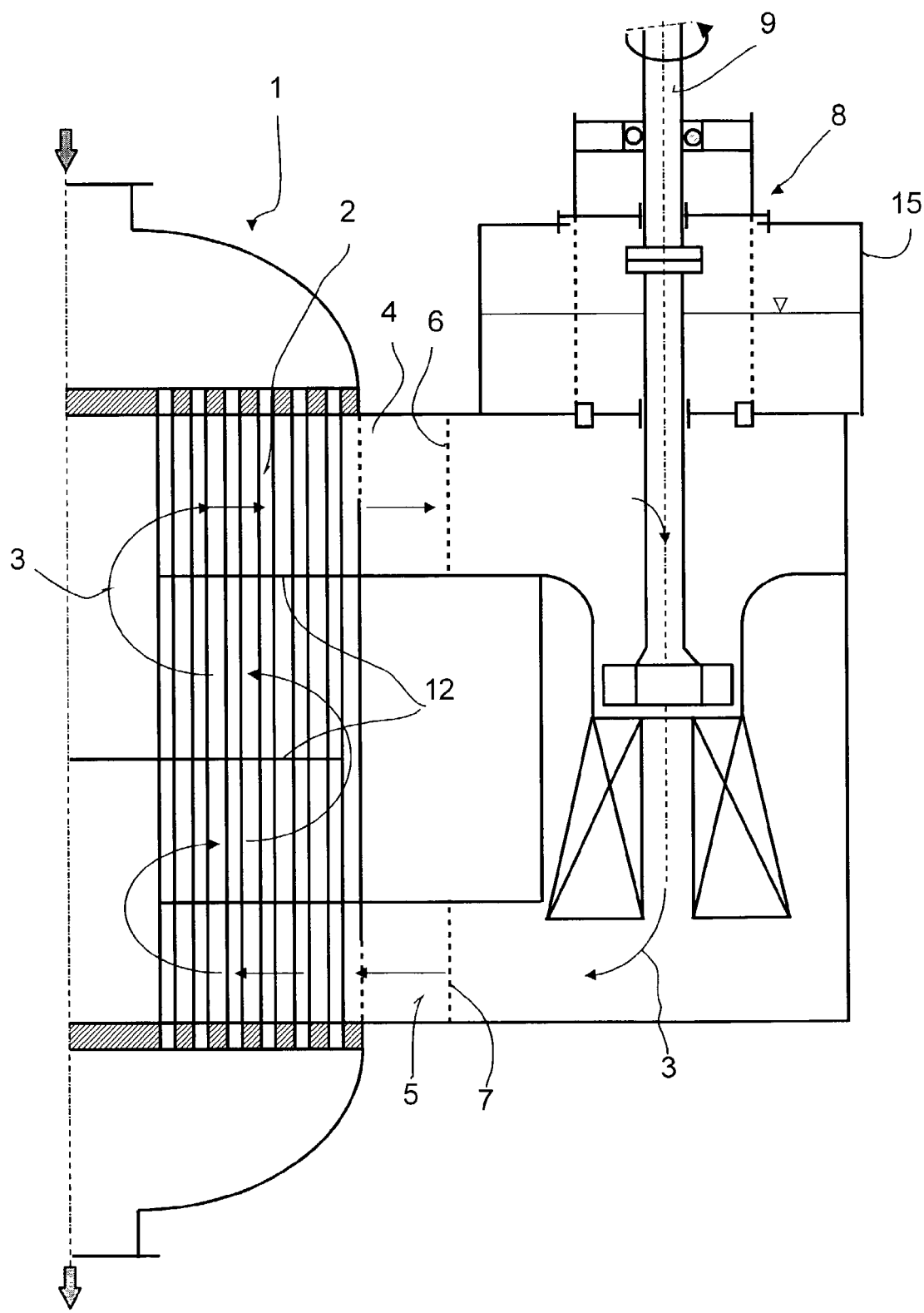

FIG. 2 on the other hand shows a longitudinal section through a reactor according to the prior art, comprising an axial-flow feed pump 8 which is in the form of a propeller pump and which transports the heat exchange medium 3 downward.

Figure 3:
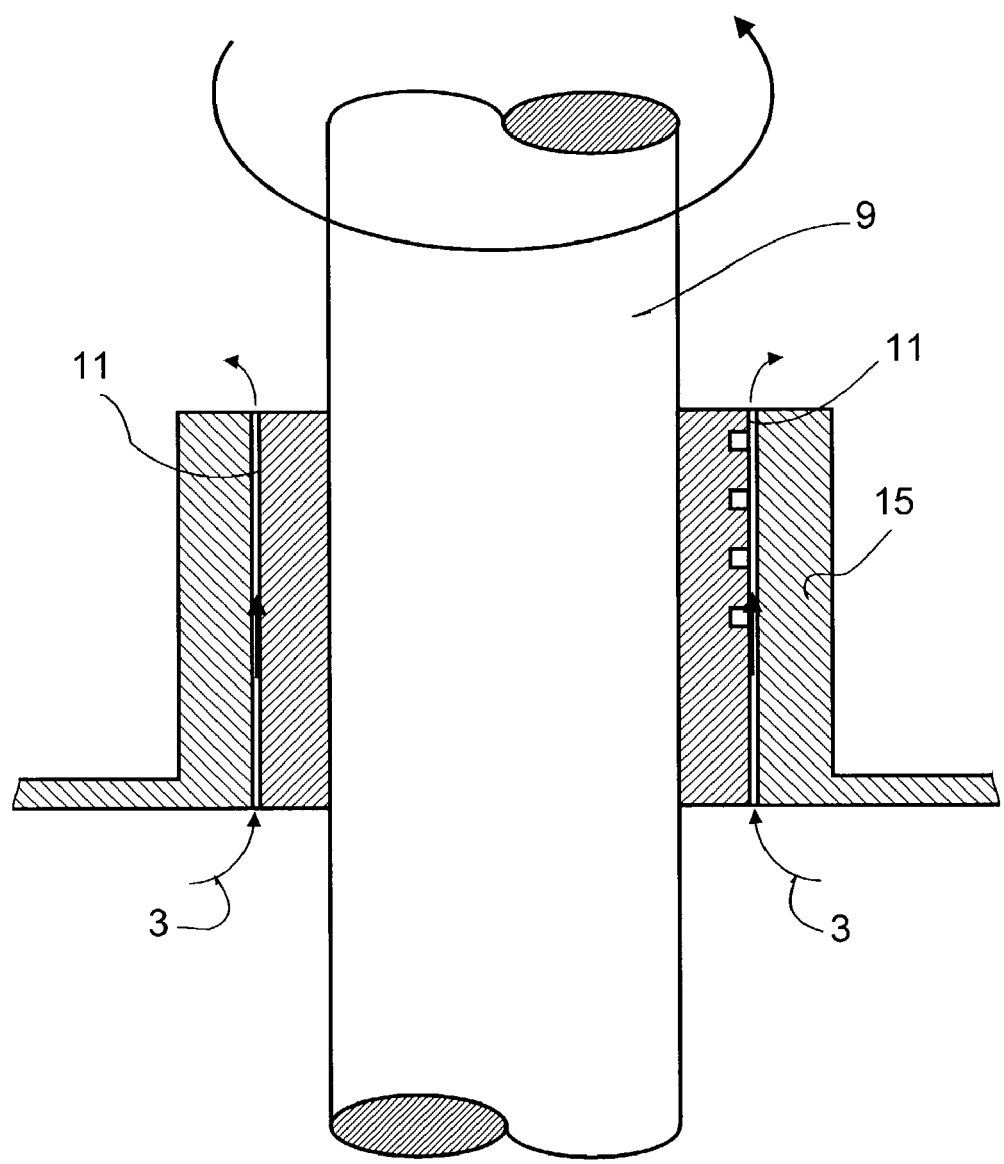
FIG. 3 shows an enlarged view of the novel restrictor gap in longitudinal section.

FIG. 3 shows an enlarged view of the leak-permeable restrictor gap 11 which allows through a leakage stream of the heat exchange medium 3 and is arranged in the longitudinal direction of the pump shaft 9.

Figure 4:
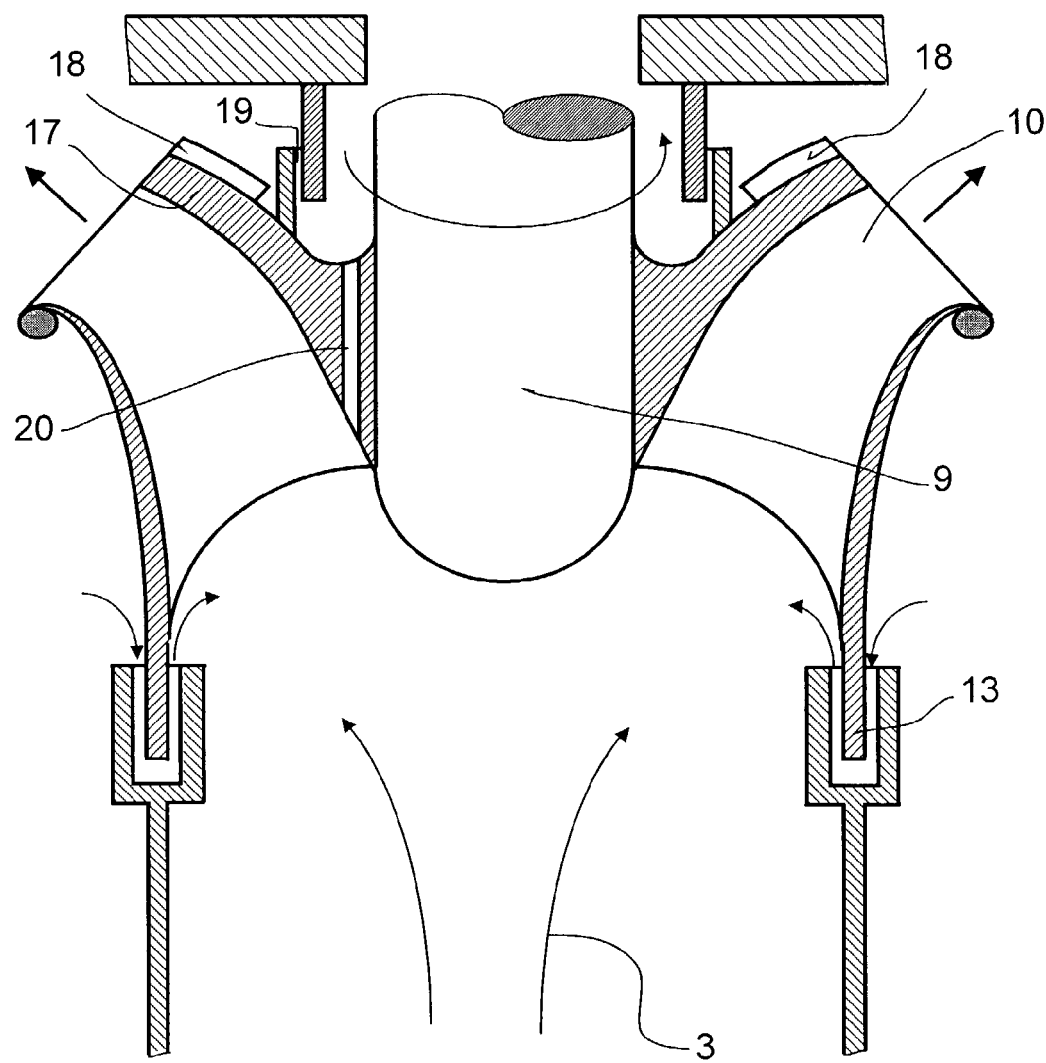
FIG. 4 shows an enlarged view of the hydrodynamic bearing at the rotor inlet in longitudinal section and FIG. 5 shows a sectional view (section D-D in the view in FIG. 4) through a pump having a pump spiral.

FIG. 4 shows, in an enlarged view, the hydrodynamic bearing 13 in the region where the heat exchange medium 3 enters the diagonal rotor 10 which is arranged on the pump shaft 9. Moreover, FIG. 4 shows additional measures on the rear disk 17 of the diagonal rotor 10: additional blades 18, an axial annular gap 19 and a relief hole 20.

Figure 5:
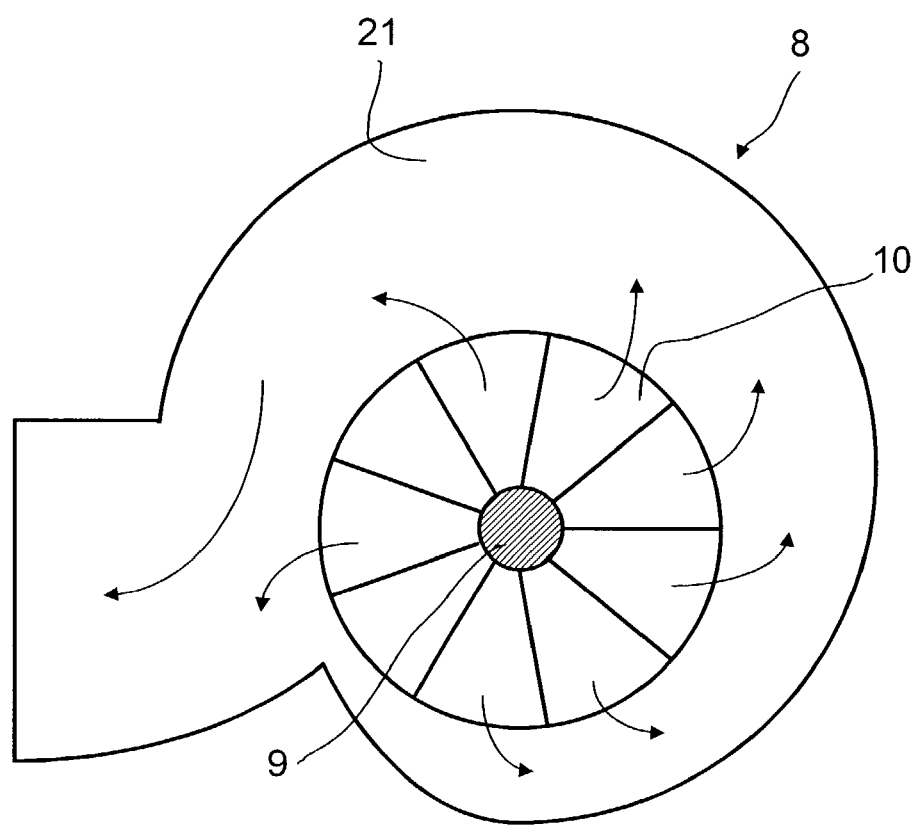

FIG. 5 shows a sectional view (section D-D in FIG. 4) through a pump 8 having a pump spiral 21.

We claim:

1. A reactor comprising:
   a bundle of catalyst tubes through which a reaction mixture is passed, and wherein a heat exchange medium is passed through a space surrounding the catalyst tubes;
   ring lines at both of reactor ends with jacket orifices for feeding in and removing the heat exchange medium by at least one pump, the heat exchange medium being fed to the upper ring line and being sucked in via the lower ring line by the at least one pump having at least one vertical pump shaft mounted and driven at its end, the pump configured to transport the heat exchange medium through the pump upwardly,
   wherein the at least one pump comprises a diagonal rotor and a leak-permeable restrictor gap, which allows a leakage stream of the heat exchange medium to pass through, upwardly in the longitudinal direction of the at least one pump shaft, within the heat exchange medium, on a pressure side of the at least one pump for sealing and mounting the at least one pump shaft and reducing axial shear of the diagonal rotor.

2. A reactor as claimed in claim 1, wherein a part-stream of the heat exchange medium is removed from the upper ring line, passed via one or more external heat exchangers and then fed back to the lower ring line.

3. A reactor as claimed in claim 1, further comprising baffle plates arranged in the reactor.

4. A reactor as claimed in claim 1, wherein a leakage stream of from 2% to 30% of the total stream of the heat exchange medium is permitted via the restrictor gap.

5. A reactor as claimed in claim 1, wherein a leakage stream of from 5% to 10% of the total stream of the heat exchange medium is permitted via the resistor gap.

6. A reactor as claimed in claim 4, wherein the leakage stream emerging from the restrictor gap is recirculated to a suction side of the at least one pump.

7. A reactor as claimed in claim 5, wherein the leakage stream emerging from the restrictor gap is recirculated to a suction side of the at least one pump.

8. A reactor as claimed in claim 1, further comprising a seal of the diagonal rotor on a suction side of the at least one pump in a form of a hydrodynamic bearing.

9. A reactor as claimed in claim 1, wherein the at least one pump includes a pump outlet spiral.

10. A reactor as claimed in claim 1, wherein the reaction mixture is passed downward through the catalyst tubes.

11. A reactor as claimed in claim 1, wherein a rear disk of the diagonal rotor includes at least two blades for decreasing the pressure in the direction of the pump shaft.

12. A reactor as claimed in claim 11, wherein an axial annular gap is formed on the back of the diagonal rotor by formation of the rear disk of the diagonal rotor and a pump casing, with sealing, mounting and axial shear reducing function.

13. A reactor as claimed in claim 11, wherein at least one relief hole from the pressure side to the suction side of the pump is provided through the rear disk of the diagonal rotor.

14. A reactor as claimed in claim 1, wherein the reaction mixture produces one of phthalic anhydride, maleic anhydride, glyoxal, (meth)acrolein, or (meth)acrylic acid.

15. A pump for circulating a heat exchange medium for a reactor including a bundle of catalyst tubes through which a reaction mixture is passed, and wherein a heat exchange medium is passed through a space surrounding the catalyst tubes, ring lines at both of reactor ends with jacket orifices for feeding in and removing the heat exchange medium by at least one pump, the heat exchange medium being fed to the upper ring line and being sucked in via the lower ring line by the at least one pump having at least one vertical pump shaft mounted and driven at its end, the pump configured to transport the heat exchange medium through the pump upwardly,
   wherein the at least one pump comprises:
   a vertical pump shaft mounted and driven at its upper end;
   a diagonal rotor; and
   a leak-permeable restrictor gap, which allows a leakage stream of the heat exchange medium to pass through, upwardly in the longitudinal direction of the pump shaft, with sealing, mounting and axial shear reducing functions.

* * * * *